(12) United States Patent
Yoon et al.

(10) Patent No.: US 12,728,270 B2
(45) Date of Patent: Sep. 8, 2026

(54) THERAPY UPGRADE SYSTEM FOR IMPLANTABLE DEVICES

(71) Applicant: Medtronic, Inc., Minneapolis, MN (US)

(72) Inventors: Hyun J. Yoon, Vadnais Heights, MN (US); James H. Borowick, Minnetrista, MN (US)

(73) Assignee: Medtronic, Inc., Minneapolis, MN (US)

( * ) Notice: Subject to any disclaimer, the term of this patent is extended or adjusted under 35 U.S.C. 154(b) by 458 days.

(21) Appl. No.: 18/187,393

(22) Filed: Mar. 21, 2023

(65) Prior Publication Data

US 2023/0321449 A1 Oct. 12, 2023

Related U.S. Application Data

(60) Provisional application No. 63/269,808, filed on Mar. 23, 2022.

(51) Int. Cl.
*A61N 1/372* (2006.01)

(52) U.S. Cl.
CPC ..... *A61N 1/37264* (2013.01); *A61N 1/37252* (2013.01)

(58) Field of Classification Search
CPC ............ A61N 1/37252; A61N 1/37254; A61N 1/37264; A61N 1/37282
See application file for complete search history.

(56) References Cited

U.S. PATENT DOCUMENTS

| | | | | |
|---|---|---|---|---|
| 7,684,861 | B2 | 3/2010 | Sanders | |
| 8,634,926 | B2 | 1/2014 | Hess et al. | |
| 9,348,974 | B2 | 5/2016 | Goetz | |
| 9,979,810 | B2 | 5/2018 | Mazar et al. | |
| 2003/0028226 | A1 | 2/2003 | Thompson et al. | |
| 2005/0192844 | A1 | 9/2005 | Esler et al. | |
| 2006/0080654 | A1* | 4/2006 | Shelton | G16H 40/40 717/173 |
| 2006/0189854 | A1 | 8/2006 | Webb et al. | |
| 2014/0019164 | A1 | 1/2014 | Armstrong | |
| 2018/0104500 | A1* | 4/2018 | Blum | A61N 1/36125 |
| 2021/0128923 | A1 | 5/2021 | Juarez Paz | |
| 2021/0316145 | A1* | 10/2021 | Offutt | A61N 1/36135 |

* cited by examiner

*Primary Examiner* — Brian T Gedeon
(74) *Attorney, Agent, or Firm* — Shumaker & Sieffert, P.A.

(57) ABSTRACT

In some examples, the disclosure describes devices, systems, and methods for determining settings of a second implantable medical device (IMD) based on patient information stored in a first IMD. The first IMD may be a device already implanted in a patient and a clinician may remove and replace the first IMD with the second IMD. The second IMD may include may be an upgrade over the first IMD (e.g., the second IMD is of the same device type but of a different model as the first IMD), may be an update to the first IMD (e.g., the second IMD is the same device type and model as the first IMD but includes different features), and/or a different device type than the first IMD.

20 Claims, 6 Drawing Sheets

THERAPY UPGRADE SYSTEM FOR IMPLANTABLE DEVICES

This application claims the benefit of U.S. Provisional Patent Application Ser. No. 63/269,808 (filed Mar. 23, 2022), which is entitled, "THERAPY UPGRADE SYSTEM FOR IMPLANTABLE DEVICES" and is incorporated by reference herein in its entirety.

TECHNICAL FIELD

The disclosure relates to medical devices, and more particularly to replacing medical devices.

BACKGROUND

Various types of implantable medical devices (IMDs) have been implanted for treating or monitoring one or more conditions of a patient. Such IMDs may be adapted to monitor or treat conditions relating to heart, muscle, nerve, brain, stomach, endocrine organs, or other organs and their related functions. Such IMDs may be associated with leads that position electrodes at a desired location, or may be leadless with electrodes integrated with and/or attached to the device housing. These IMDs may have the ability to wirelessly transmit data either to another device implanted in the patient or to another instrument located externally of the patient, or both.

SUMMARY

In general, the present disclosure describes devices, systems, and methods for optimizing implantable medical device (IMD) changeout or upgrade. For instance, a patient implanted with a current IMD (e.g., a first IMD) may have the current IMD removed, and implanted with another IMD (e.g., second IMD). For instance, the second IMD may be an upgrade over the first IMD (e.g., the second IMD includes more robust features than the first IMD), or may be a different class of IMD (e.g., first IMD is a sensing device, and the second IMD is a sensing device with therapy delivery capabilities).

For upgrade or changeout, there may be information generated by and/or stored on the first device (e.g., the device being removed) that may enhance the operation of the second device (e.g., the device being implanted). This disclosure describes example techniques to extract information from or generated by the first device, and using the extracted information for programming the second device. In this way, the example techniques may allow for seamless transition from the first device to the second device, while optimizing the usage of the features of the second device.

For example, processing circuitry may be configured to receive patient information from a first IMD with a first set of features, determine one or more settings for a different set of features of a second IMD using the patient information, and configure the second IMD based on the determined settings. The second IMD may be an upgraded IMD of the same device type as the first IMD or may be of a different device type than the first IMD. By using patient information from the first IMD to determine the one or more settings for the second IMD, the devices, systems and methods of this disclosure may facilitate a faster and more efficient implantation process and may also facilitate improved, individualized, programming of IMDs.

In some examples, the disclosure describes a system for therapy upgrade, the system comprising: a memory; and processing circuitry coupled to the memory, the processing circuitry being configured to: receive patient information generated with a patient having a first implantable medical device, the first implantable medical device having a first set of features; determine one or more settings for a second set of features of a second implantable medical device, the second set of features are different than the first set of features; and configured the second implantable medical device based on the determined one or more settings.

In some examples, the disclosure describes a method for therapy upgrade, the method comprising: retrieving, by processing circuitry, patient information generated with a patient having a first implantable medical device, the first implantable medical device having a first set of features; determining, by the processing circuitry, one or more settings for a second set of features of a second implantable medical device, the second set of features are different than the first set of features; and configuring, by the processing circuitry, the second implantable medical device based on the determined one or more settings.

In some examples, the disclosure describes a computer readable storage medium comprising instructions that, when executed, cause one or more processors to perform a method for therapy upgrade, the method comprising: retrieving, by processing circuitry, patient information generated with a patient having a first implantable medical device, the first implantable medical device having a first set of features; determining, by the processing circuitry, one or more settings for a second set of features of a second implantable medical device, the second set of features are different than the first set of features; and configuring, by the processing circuitry, the second implantable medical device based on the determined one or more settings.

In some examples, the disclosure describes a device for therapy upgrade, the device comprising: means for retrieving patient information generated with a patient having a first implantable medical device, the first implantable medical device having a first set of features; means for determining one or more settings for a second set of features of a second implantable medical device, wherein the second set of features are different than the first set of features; and means for configuring the second implantable medical device based on the determined one or more settings.

This summary is intended to provide an overview of the subject matter described in this disclosure. It is not intended to provide an exclusive or exhaustive explanation of the methods and systems described in detail within the accompanying drawings and description below.

BRIEF DESCRIPTION OF THE DRAWINGS

The details of one or more examples of this disclosure are set forth in the accompanying drawings and the description below. Other features, objects, and advantages of this disclosure will be apparent from the description and drawings, and from the claims. Reference is made to the attached drawings, wherein elements have the same reference numeral designations represent similar elements throughout.

DETAILED DESCRIPTIONS

In general, the present disclosure describes devices, systems, and methods for determining settings of a second implantable medical device (IMD) based on patient information stored in or generated by a first IMD. The first IMD may be a device already implanted in a patient and a clinician may remove and replace the first IMD with the second IMD. The second IMD may be an upgrade over the first IMD (e.g., the second IMD is of the same device type but of a different model as the first IMD), may be an update to the first IMD (e.g., the second IMD is the same device type and model as the first IMD but includes different features), and/or a different device type than the first IMD.

In some examples, as the health status of a patient changes, a clinician may need to replace a prior IMD with a new IMD to address the changing needs of the patient. For example, as the severity of an illness progresses, the clinician may wish to replace an implantable monitoring device with an implantable therapy delivery device. In some examples, the clinician may wish to replace an older IMD with a newer IMD or update the software and/or firmware of the IMD to provide the patient access to new and/or improved features. Traditionally, during implantation of an IMD, a clinician manually enters the settings for the features of the IMD. The manual programming of the IMD may be a time-consuming process and may be prone to errors. Additionally, the new feature programming may not be optimally configured due to the limited clinical information the clinician may have access to.

The devices, systems, and methods of this disclosure may offer technological improvement over the usage of an implantable device (e.g., a second IMD) that is replacing a current implantable device (e.g., a first IMD) such as by determining the optimal settings of a second IMD based on patient information stored in or generated by a first IMD. In some examples, the devices, systems, and methods of this disclosure may reduce the amount of manual inputs a clinician enters to program the second IMD and may reduce the overall implantation time and the number of programming errors due to human error. In some examples, the devices, systems, and methods of this disclosure may determine settings for the second IMD that are better optimized for the patient's specific needs than manually-inputted settings since the determined settings are generated based on the patient's clinical information that is generated by and/or stored in the first IMD. In some examples, by determining the optimal settings of the second IMD at the time of implantations, the devices, systems, and methods, of this disclosure may provide an optimal treatment to the patient through the second IMD without requiring the second IMD to record patient information and determine the optimal settings over a long period of time (e.g., a few months).

Figure 1:
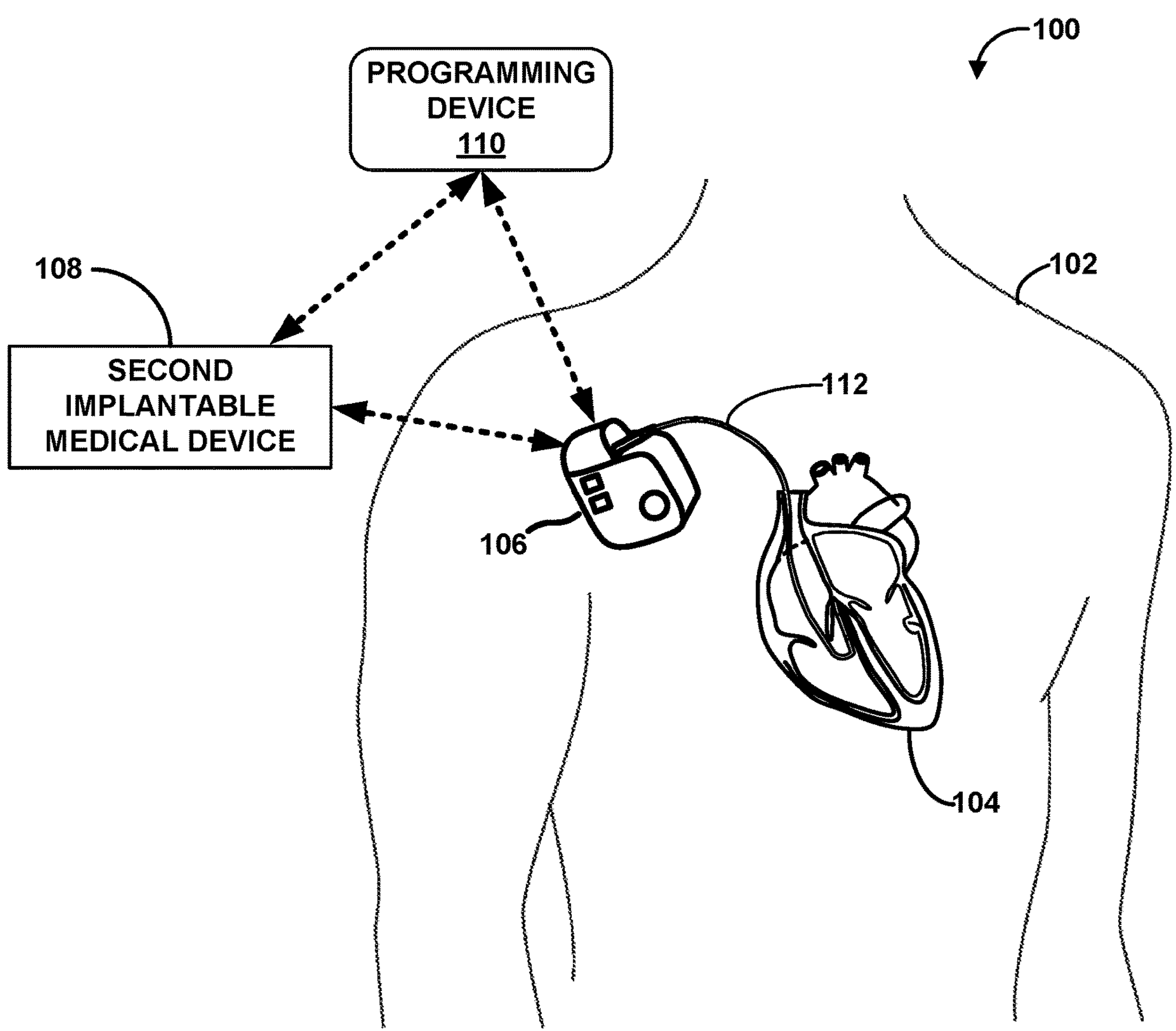
FIG. 1 is a conceptual illustration of an example therapy upgrade system, in accordance with one or more aspects of this disclosure.

FIG. 1 is a conceptual illustration of an example therapy upgrade system 100, in accordance with one or more aspects of this disclosure. While therapy upgrade system 100, as illustrated in FIG. 1, is illustrated with cardiovascular-related IMDs, the devices, systems and methods of this disclosure may be directed to other IMDs, e.g., deep brain stimulation (DBS), spinal cord stimulation (SCS), pelvic stimulation, gastric stimulation, or peripheral nerve field stimulation (PNFS), as few additional examples. Therapy upgrade system 100 may include a first IMD 106 implanted in patient 102 and electrically connected to heart 104 through electrical leads 112, a second IMD 108, and a programming device 110. First IMD 106 may include a first set of features and second IMD 108 may include a second set of features. In some examples, the sets of features may include device functionalities (e.g., sensing, stimulation, therapy delivery), special operating modes (e.g., operating modes for operation in the presence of a Magnetic Resonance Imaging (MRI) device, single-chamber mode, dual-chamber mode), and the like.

First IMD 106 and second IMD 108 may be selected from a plurality of device models for different implantable device types. The implantable device types may include implantable cardiac monitors (ICM), implantable pulse generators (IPG), implantable defibrillators implantable cardioverter defibrillators (ICD), cardiac resynchronization therapy (CRT) devices, and the like. In some examples, second IMD 108 may be of a different device type than first IMD 106. For example, first IMD 106 may be an ICM and second IMD 108 may be an IPG. In other examples, second IMD 108 may be of a same device type but of a different device model than first IMD 106. In other examples, second IMD 108 may be of the same device type and model as first IMD 106 but include different software. In other examples, second IMD 108 may be the same physical device as first IMD 106 but include different software such that previously unavailable features are made available.

In some examples, first IMD 106 may be currently implanted in patient 102 and the implantation procedure may involve surgically removing first IMD 106 from patient 102 and implanting second IMD 108 into patient 102, such as in examples where first IMD 106 and second IMD 108 are different devices. In other examples, first IMD 106 may have already been removed for a period of time and the implantation procedure may only involve implanting second IMD 108 into patient 102. In other examples, the implantation procedure may only involve removing first IMD 106 and second IMD 108 may be implanted into patient 102 in a later, separate implantation procedure.

During the implantation procedure, programming device 110 may retrieve, from the memory of first IMD 106, patient information. There may be other locations from which programming device 110 may retrieve patient information, such as patient information stored in a cloud computing environment. Patient information may include patient health parameters (e.g., prior recorded cardiac episodes, clinical records, pacing thresholds, sensing thresholds, and the like), changes in the patient health parameters, and/or first IMD 106 device settings for the features of first IMD 106 (e.g., device settings, therapy settings, device trends, electrical lead information, and the like).

Programming device 110 may determine optimal settings for the second set of features of second IMD 108 based on the retrieved patient information. In some examples, programming device 110 may predict, based on the retrieved patient information, a probable progression of the health of the patient and may determine the settings for the second set of features of second IMD 108 to properly address the potential progression of the health of the patient. For example, programming device 110 may determine, based on the progression of a cardiovascular disease of the patient, that second IMD 108 needs to deliver more aggressive stimulation therapy. In response, programming device 110 may determine settings for the second set of features that may facilitate second IMD 108 delivering more aggressive stimulation therapies. In some examples, the second set of features are completely different from the first set of features. In other examples, one or more features of the second set of features may also be included in the first set of features.

In some examples, second IMD 108 may retrieve and/or extract the patient information directly from first IMD 106. Second IMD 108 may analyze the retrieved patient information and optimize the second set of features. In some examples, second IMD 108 may determine, based on the retrieved patient information, that second IMD 108 needs to deliver a more aggressive or a more conservative stimulation therapy. In response, second IMD 108 may determine settings for the second set of features to deliver the appropriate stimulation therapies.

For example, first IMD 106 may be configured to sense cardiac signals for diagnostic purposes, but may not be configured to deliver therapy. Second IMD 108 may be configured to delivery therapy (e.g., defibrillation pulses, cardiac resynchronization therapy, etc.). Accordingly, second IMD 108 may include features that are not present in first IMD 106. As another example, first IMD 106 may be configured to sense cardiac signals, and second IMD 108 may also be configured to sense cardiac signals, but in a way that further minimizes noise as compared to first IMD 106. In this example, the sense features of second IMD 108 may not be present in first IMD 106, even though first IMD 106 is configured to sense cardiac signals.

In some examples, the lifetime data and information of patient 102 may be transferred from one IMD to another IMD and/or a computing device or system to maintain a singular history of patient 102. In some examples, second IMD 108 may amend and/or add to the patient information and may transmit the updated patient information to a third IMD, e.g., for a next stage in the treatment of the patient. The devices, systems, and methods of this disclosure may utilize the singular history of patient 102 to facilitate the transitions between the IMDs (e.g., from first IMD 106 to second IMD 108, from second IMD 108 to the third IMD, and the like).

In some examples, the settings for the features of first IMD 106 and second IMD 108 may include therapy settings (e.g., amplitude, pulse width, sensitivity, and the like for a stimulation signal), IMD sensing settings, (e.g., upper sensor rate, lower sensor rate, and the like), patient health parameters (e.g., average heart rate, recorded cardiac irregularities), patient health parameter trends (e.g., recent changes in patient's average heart rate, increasing detection of cardiac irregularities), and the like. IMD sensor data including previous history and configuration settings. IMD Therapy optimization (e.g., detection discrimination parameters and settings, therapy parameters, configuration and settings). IMD Protection (e.g., environmental conditions).

In some examples, programming device 110 may update first IMD 106 to include new software, firmware, and/or programming. In some examples, programming device 110 may enable previously unavailable and/or disabled features in first IMD 106. Based on the patient information, programming device 110 may determine the optimal settings for the newly available features and apply the features to first IMD 106.

Programming device 110 may determine the optimal settings for the second set of features of the second IMD 108 by determining the optimal application of the feature to address the patient's conditions based on the patient information generated by or stored on first IMD 106, and determining the optimal settings corresponding to the optimal application. In some examples, programming device 110 may determine the optimal settings using a machine learning technique, e.g., by apply the machine learning technique to a dataset of past patient information and corresponding feature settings for the past patients.

After programming device 110 determines the optimal settings, programming device 110 may transmit the optimal settings to the second IMD 108, e.g., through a temporary update file. Programming device 110 may configure the second IMD 108 based on the determined settings for the features of second IMD 108. In some examples, programming device 110 may be configured to wirelessly communicate with first IMD 106 and second IMD 108. In some examples, programming device 110 may be configured to communicate with first IMD 106 and second IMD 108 via one or more electrical wires. In some examples, first IMD 106 may transmit the stored patient information to a cloud computing environment (e.g., cloud storage) and programming device 110 may retrieve the stored patient information from the cloud computing environment to determine the settings for the second set of features.

Although the example techniques are described with respect to programming device 110, the example techniques are not so limited. For instance, in some examples, second IMD 108 may be configured to perform the example techniques of determining the settings to implement the features of second IMD 108 using information determined by IMD 106. As another example, processing circuitry in a cloud computing environment may be configured to perform the example techniques of determining the settings to implement the features of second IMD 108 using information determined by IMD 106. For example, IMD 106 may upload information to the cloud computing environment (e.g., via programming device 110). The cloud computing environment may determine settings to implement the features of second IMD 108, transmit the settings to programming device 110, that transmits the settings to second IMD 108.

Figure 2:
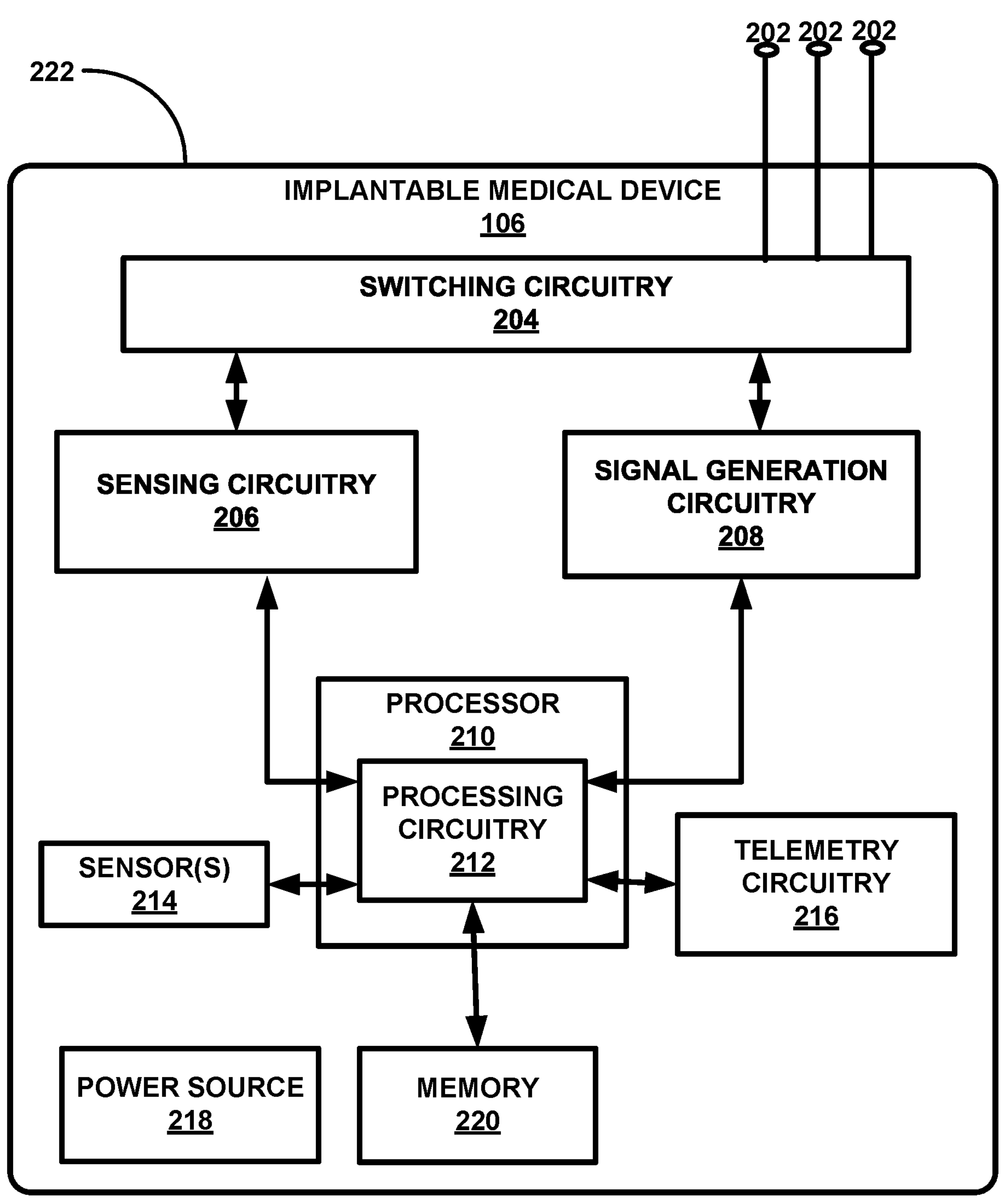
FIG. 2 is a functional block diagram illustrating an example configuration of the IMD of FIG. 1.

FIG. 2 is a functional block diagram illustrating an example configuration of the first IMD 106 of FIG. 1. The configuration of first IMD 106, as illustrated in FIG. 2, is directed at a generic IMD. In other examples, first IMD 106 may include different circuitry and elements based on the device type and device model of first IMD 106. In some examples, the circuitry and elements of second IMD 108 may be substantially similar to the circuitry and elements of first IMD 106. The various functions of the respective circuitry of first IMD 106 is described with respect to heart 104 of patient 102, but the functions may be configured to perform other functions with respect to heart 104 and/or other anatomical structures of patient 102, depending on the device type and device model of first IMD 106.

In the example shown in FIG. 2, first IMD 106 includes a plurality of electrodes 202, switching circuitry 204, sensing circuitry 206, signal generation circuitry 208, processor 210 including processing circuitry 212, sensors 214, telemetry circuit 216, power source 218, memory 220, and housing 222. The various circuitry may be, or include, programmable or fixed function circuitry configured to perform the functions attributed to the respective circuitry. Memory 220 may store computer-readable instructions that, when executed by processor 210, cause first IMD 106 to perform various functions. Memory 220 may be a storage device or other non-transitory medium. The components of first IMD 106 illustrated in FIG. 2 may be housed within housing 222. The electrodes 202 may be configured to electrically connect signal generation circuitry 204 to heart 104, e.g., by penetrating into tissue of heart 104 or by maintaining contact with the tissue of heart 104.

Signal generation circuitry 208 may be configured to generate stimulation signals, e.g., cardiac pacing pulses, to heart 104 through electrodes 202. Signal generation circuitry 208 may include, as examples, current or voltage sources, capacitors, charge pumps, or other signal generation circuitry. Signal generation circuitry 208 may be connected to switching circuitry 204. Switching circuitry 204 may be configured to direct the stimulation signals from signal generation circuitry 208 to a selected combination of electrodes 202. In some examples switching circuitry 204 may selectively couple sensing circuitry 206 to electrodes 202 to sense electrical activity of heart 104. Sensing circuitry 206 may include filters, amplifiers, analog-to-digital converters, or other circuitry configured to sense electrical signals via electrodes 202. In some examples, sensing circuitry 206 is configured to detect certain events within the sensed electrical signals and provide indications to processor 210. In some examples, sensing circuitry 206 is configured to record cardiac activity (e.g., heart rhythm activity) through electrodes 202.

Processor 210 may include processing circuitry 212 including one or more microprocessors, controllers, digital signal processors (DSP), application specific integrated circuits (ASIC), field-programmable gate array (FPGA), discrete logic circuitry, or any other processing circuitry configured to provide the functions attributed to processing circuitry 212 herein. Processor 210 may be embodied as firmware, hardware, software, or any combination thereof.

Processing circuitry 212 may be configured to record patient information, (e.g., patient health parameters and/or first IMD 106 device settings) and store the patient information in memory 220. In some examples, processor 210 may be configured to send to signal generation circuitry 208 and/or switching circuitry 204 instructions to modify one or more stimulation signals.

Sensor(s) 214 may include one or more sensing elements that transduce patient physiological activity to an electrical signal to sense values of a respective patient parameter. Sensor(s) 214 may include one or more accelerometers, optical sensors, chemical sensors, temperature sensors, pressure sensors, or any other types of sensors. Sensor(s) 214 may output patient health parameters and may store the patient health parameters in memory 220.

Telemetry circuitry 216 supports wireless and/or wired communication between first IMD 106 and programming device 110, another computing device, or to a cloud computing environment. In some examples, processor 212 of first IMD 106 may send, via telemetry circuitry 216, patient information to programming device 110. In some examples, processor 212 of first IMD 106 (or of IMD 108) may receive, via telemetry circuitry 216, settings to the set of features of first IMD 106 (or of IMD 108) and processor 212 may configure the set of features based on the received settings. Telemetry circuitry 216 may accomplish communication with programming device 110 by radiofrequency (RF) communication techniques, e.g., via an antenna (not shown), or by wired communication techniques.

Although first IMD 106 is illustrated with having sensing and stimulation (e.g., therapy delivery) capabilities, the example techniques are not so limited. For instance, IMD 106 may be one of an implantable cardiac monitor (ICM) device, an implantable pulse generator (IPG) device, an implantable cardioverter defibrillator (ICD) device, or cardiac resynchronization therapy (CRT) device. In some examples, an upgrade to first IMD 106 may be available, such as with replacement with second IMD 108, with update to the firmware/software of first IMD 106, or by allowing access to previously hidden features of first IMD 106. In this disclosure, replacing IMD 106 with second IMD 108 or upgrading (e.g., updating firmware or software or allowing access to previously hidden features) may be considered as IMD 106 being replaced by second IMD 108.

During operation IMD 106 may have generated information (e.g., sensed or otherwise determined). When first IMD 106 is replaced by second IMD 108, the information generated by first IMD 106 may be useful to optimize the features of second IMD 108. For instance, signals sensed by sensing circuitry 206 and stored in memory 220 may be useful for programming therapy parameters of therapy that second IMD 108 delivers that first IMD 106 may not be able to deliver. For example, assume that signal generation circuitry 208 is configured to deliver pacing pulses and cannot deliver a defibrillation signal, but second IMD 108 is configured to deliver a defibrillation signal.

In one or more examples, signals sensed by sensing circuitry 206 and stored in memory 220 may provide an initial baseline for when second IMD 108 is to deliver defibrillation signal. However, the signals sensed by sensing circuitry 206 and stored in memory 220 may be lost when first IMD 106 is replaced by second IMD 108. Without the information generated by first IMD 106, the defibrillation feature of IMD 108 may be suboptimal because second IMD 108 may not include the information of the signals sensed by sensing circuitry 206.

In some examples, first IMD 106 may transmit the signals sensed by sensing circuitry 206 and stored in memory 220 to a programming device (e.g., programming device 110), e.g., via telemetry circuitry 216. Programming device 110 may use the information generated by first IMD 106 to determine optimal settings for the features of second IMD 108 (e.g., defibrillation feature of second IMD 108). The settings determined by programming device 110 may be optimal for patient 102 because the settings incorporate the signals sensed by sensing circuitry 206 of first IMD 106 and thus account for the physiological conditions of patient 102.

Figure 3:
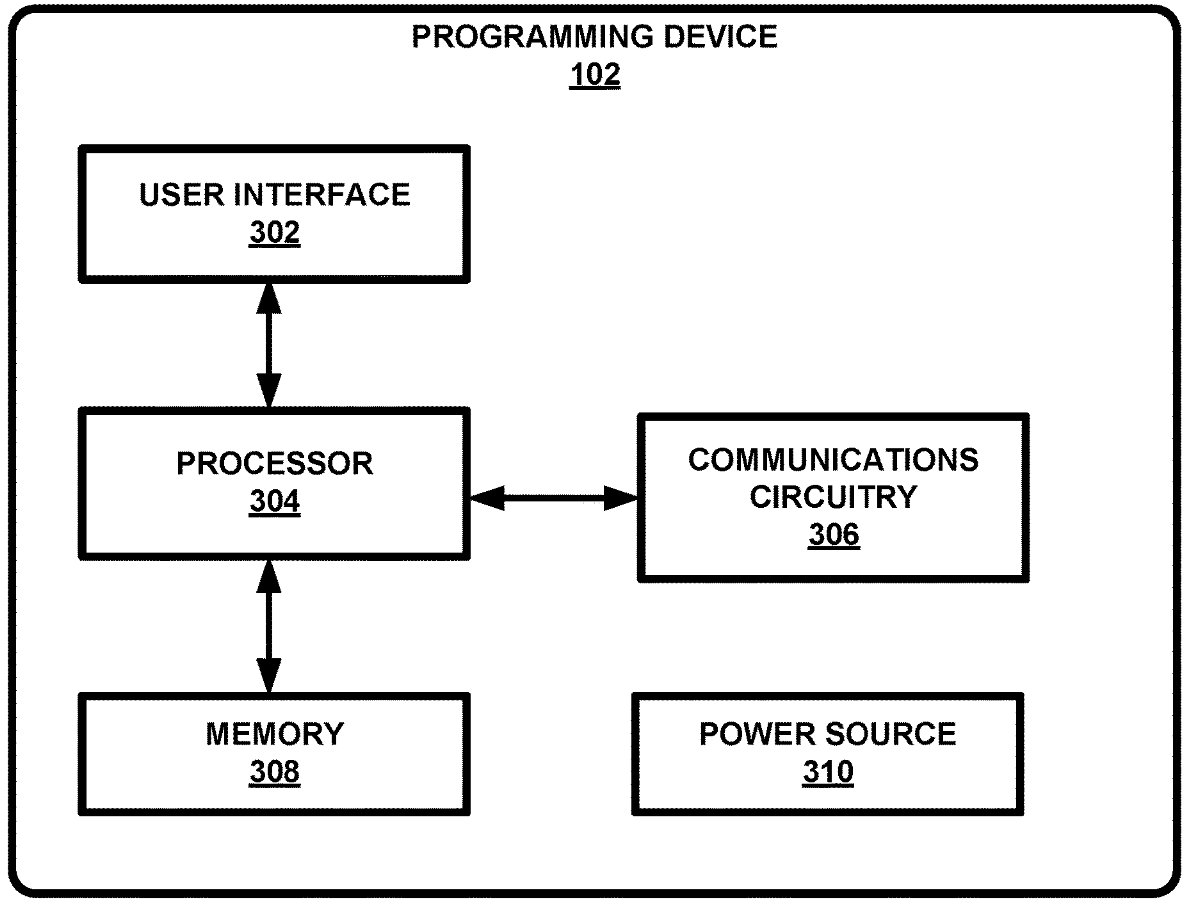
FIG. 3 is a functional block diagram illustrating an example configuration of the programming device of FIG. 1.

FIG. 3 is a functional block diagram illustrating an example configuration of the programming device 110 of FIG. 1. Programming device 110 may include user interface (UI) 302, processor 304, communications circuitry 306, memory 308, and power source 310. UI 302 may transmit information and/or retrieve data and instructions from a user, such as a patient or a clinician. UI 302 may transmit to the user a selectable menu providing a plurality of therapy upgrade options. The therapy upgrade options may include options for changing the device type ("device change out"), changing the device model ("device upgrade"), and changing the device software ("device update"). UI 302 may receive from the user a selection indicating the device type and/or model of first IMD 106 and the device type and/or model of second IMD 108. In some examples, UI 302 may also receive from the user a plurality of desired settings for the second set of features of second IMD 108 (e.g., an indication to include a MRI-safe mode).

In some examples, UI 302 may display patient information that is retrieved from first IMD 106. In some examples, UI 302 may display an initial set of settings for the second set of features of second IMD 108. The initial set of settings may be pre-populated by processor 304 based on the retrieved patient information from first IMD 106.

In some examples, if first IMD 106 is of a same device type as second IMD 108, processor 304 may directly transfer the values of all applicable parameters from first IMD 106 to second IMD 108. In some examples, processor 304 may determine nominal values for new features in the initial set of settings for the second set of features. In some examples, processor 304 may determine nominal values the second set of features based on past patient information which may be stored in memory 308 (e.g., data on past episodes, patient heart rate history, patient dominant rhythm, patient episode history, patient activity history, and the like). In some examples processor 304 may determine the nominal values based on past diagnoses of patient 102 by healthcare professionals.

Processor 304 may receive the patient information from first IMD 106 (e.g., from telemetry circuitry 216 of first IMD 106 to communications circuitry 306 of programming device 110) and/or a cloud computing environment (e.g., via communications circuitry 306 of programming device 110). Based on the patient information, processor 304 may convert and optimize the patient information into a compatible format for second IMD 108 and determine an initial set of settings for the second set of features of second IMD 108. In some examples, processor 304 may convert the received patient information using one or more conversion tables stored in memory 308, one or more defined data standards, or the like. In some examples, processor 304 may perform the conversion and optimization using a machine learning technique such as, but is not limited to, regression analysis, neural network analysis, and the like. In some examples, an operator (e.g., programmer) may train the machine learning model using a dataset of past patient information and corresponding feature settings. In one example, with regard to cardiovascular devices, if first IMD 106 is a sensing device and second IMD 108 is a defibrillation device, processor 304 may determine an initial set of settings for the detection parameters of second IMD 108 and then optimize the settings for the detection parameters of second IMD 108 based on patient information retrieved from first IMD 106. For example, if the patient information indicates that first IMD 106 sensed a high frequency of atrial fibrillation in patient 102, processor 304 may adjust the settings of second IMD 108 to operate in a battery saving mode and to not constantly monitor atrial fibrillation in patient 102.

Memory 308 may store patient information received by programming device 110 from a user, first IMD 106, second IMD 108, and/or cloud computing environment. In some examples, memory 308 may store instructions for processor 304 to convert and optimize the patient information and determine the optimal settings for the second set of features of second IMD 108. In some examples, processor 304 may save the optimal settings into a temporary save file and store the temporary save file into memory 308. Processor 304 may save the optimal settings into a temporary save file to maintain the security of first IMD 106 and/or second IMD 108. The temporary save files may reduce the likelihood of unauthorized access and changes to first IMD 106 and/or second IMD 108 and unauthorized access and use of patient information stored in memory 308. In some examples, processor 304 may delete the temporary save file from memory 308 based on a determination that the temporary save file has not been uploaded to second IMD 108 within a set period (e.g., within six hours). Power source 310 provides power to the other components of programming device 110. Power source 310 may be rechargeable and/or removable.

Figure 4:
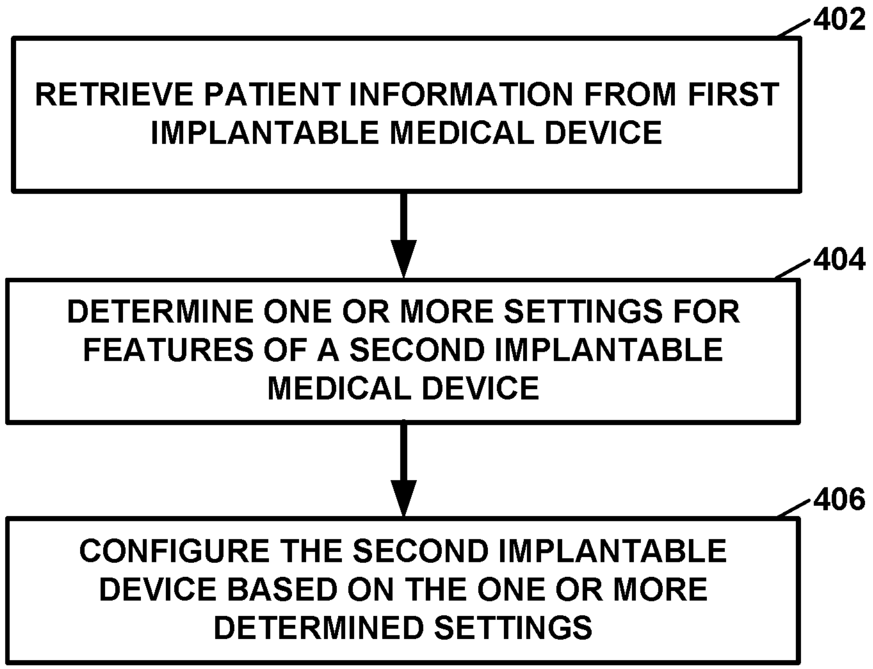
FIG. 4 is a flow chart illustrating an example method of configuring a second IMD based on patient information from the first IMD.

FIG. 4 is a flow chart illustrating an example method of configuring a second IMD 108 based on patient information from the first IMD 106. The example method illustrated in FIG. 4 may be performed by programming device 110, by second IMD 108, through cloud computing, or by one or more other computing devices and/or systems.

Programming device 110 first retrieves patient information from a first implantable medical device (e.g., first IMD 106) (402). In some examples, programming device 110 may transmit an instruction to first IMD 106 to transmit the patient information to programming device 110 and store the patient information into memory 220 upon receiving the patient information from first IMD 106. Programming device 110 may transmit the instructions to first IMD 106 and retrieve patient information from first IMD 106 through communications circuitry 306 of programming device 110. In some examples, first IMD 106 may transmit the patient information to a cloud computing environment and programming device 110 may retrieve the patient information from the cloud computing environment. Patient information may include patient health parameters and the settings for the first set of features of first IMD 106. In some examples, programming device 110 may retrieve patient information from first IMD 106 during an implantation procedure, e.g., in an operating room. In other examples, programming device 110 may retrieve the patient information while first IMD 106 is still implanted in a patient, e.g., as part of a scheduled device inspection and/or update.

Programming device 110 may determine one or more settings for a second set of features of a second implantable medical device (e.g., second IMD 108) (404). Programming device 110 may convert patient information into a format (e.g., another digital format) that is readable by second IMD 108. Programming device 110 may determine the optimal settings for the second set of features by applying a machine learning technique to the retrieved patient information. In some examples, programming device 110 may determine the optimal settings based on current and future patient requirements, as indicated by the patient information. In some examples, programming device 110 may first determine the optimal application of the second set of features to the patient based on the patient information and later determine the optimal settings to instruct second IMD 108 to deliver the optimal application to the patient. For example, programming device 110 may determine an optimal application of the second set of features in response to a patient activity (e.g., exercise). Programming device 110 may then determine the optimal settings (e.g., a rate of adjustment between therapy modes) for second IMD 108 to deliver the optimal application to the patient.

Programming device 110 may configure the second IMD 108 based on the one or more determined settings (406). In some examples, programming device 110 may transmit the determined settings into a processor (e.g., processor 210) of second IMD 108 and instruct processor 210 to adjust the second set of features based on the determined settings. For example, programming device 110 may transmit to processor 210 determined settings regarding the parameters of a therapy feature (e.g., stimulation signal amplitude, stimulation signal frequency, and the like) and instruct processor 210 to use the determined settings to program the therapy feature (e.g., by using the determined settings as input values during a programming step of the implantation procedure). In some examples, programming device 110 may determine, based on the determined settings, a desired configuration for second IMD 108 through the application of a machine learning technique. Programming device 110 may then instruct processor 210 of second IMD 108 to modify the second set of features to comply with the desired configuration. In some examples, programming device 110 may generate and output to processor 210 a temporary save file based on the determined settings which, when executed, cause processor 210 to automatically modify the parameters of the second set of features to generate the optimal application of the second set of features.

Figure 5:
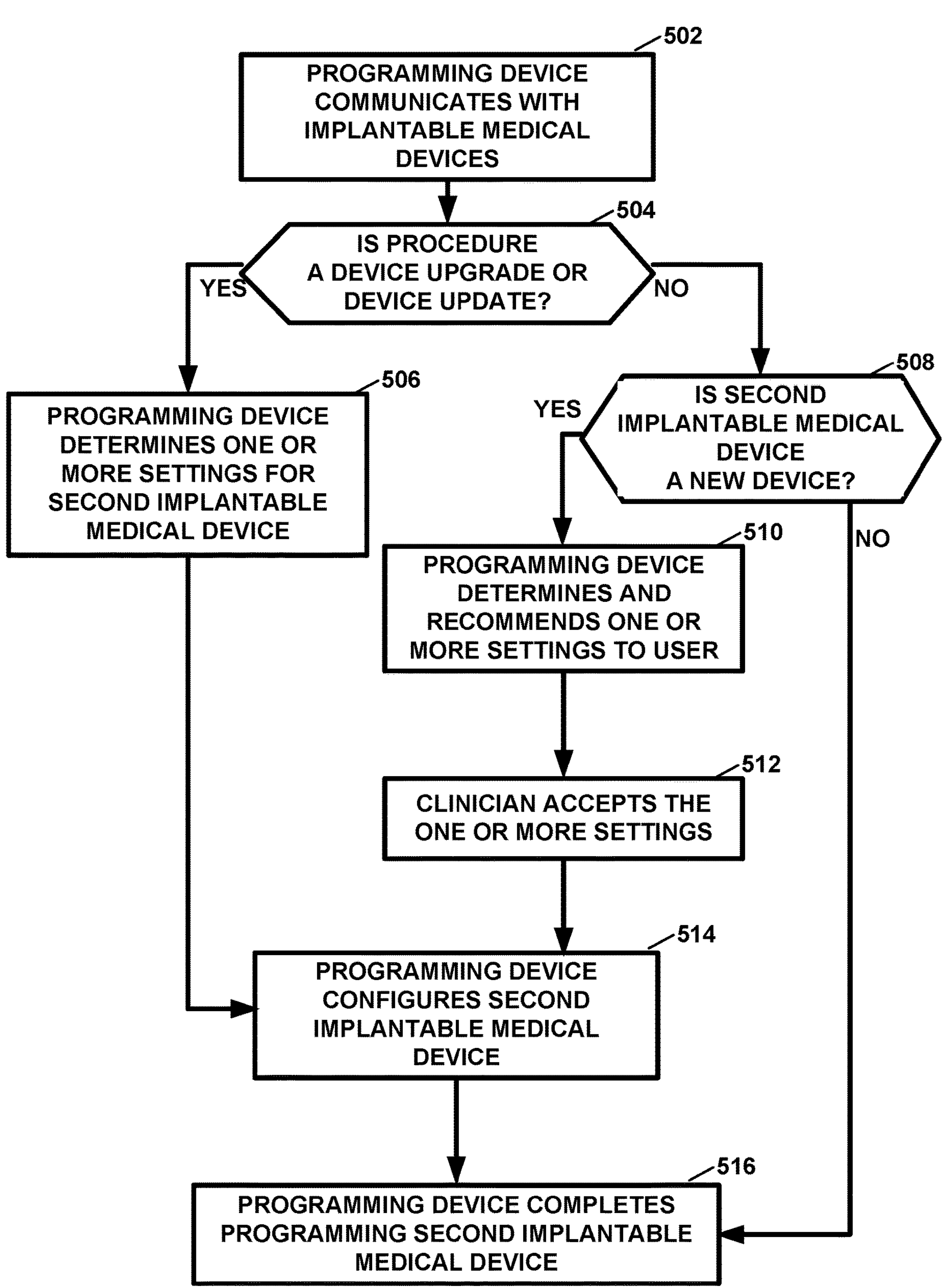
FIG. 5 is a flow chart illustrating another example method of configuring a second IMD based on patient information from the first IMD.

FIG. 5 is a flow chart illustrating another example method of configuring a second IMD based on patient information from the first IMD. Programming device 110 may communicate with implantable medical devices (e.g., first IMD 106, second IMD 108) (502). Programming device 110 may communicate with first IMD 106 and second IMD 108 either wirelessly or through a wired connection. In some examples, programming device 110 may be communicating with both first IMD 106 and second IMD 108 simultaneously. In other examples, programming device 110 may first communicate with first IMD 106 and then communicate with second IMD 108. In some examples, programming device 110 may also be in communication with a cloud computing environment while it is in communication with either first IMD 106 or second IMD 108. In some examples, while communicating with first IMD 106 or the cloud computing environment, programming device 110 may receive patient information, e.g., from first IMD 106 or the cloud computing environment.

Programming device 110 may determine if the implantation procedure is a device upgrade, where second IMD 108 is of a same device type but of a different model first IMD 106, or a device update, where second IMD 108 is the same physical device as first IMD 106 but including updated software and/or firmware (504). Programming device 110 may determine the type of implantation procedure through user input, e.g., via UI 302.

Based on a determination that the implantation procedure is either a device upgrade or a device update ("YES" branch of 504), programming device 110 may determine one or more settings for second IMD 108 (506), e.g., in accordance with the example method of FIG. 4. Once programming device has determined the settings for second IMD 108, programming device 110 may configure second IMD 108 using the determined settings (514). Once configuration is complete, programming device 110 may complete programming second IMD 108 (516). Completing programming second IMD 108 may include saving any changes to second IMD 108 and notify user that programming is complete.

If programming device 110 determines that the implantation procedure is neither a device upgrade nor a device change out ("NO" branch of 504), programming device 110 may determine if second IMD 108 is a new device (508) based on user input, e.g., via UI 302. A new device may indicate that the implantation procedure is a device change out, where second IMD 108 is of a different device type than first IMD 106. An old device may indicate that the replacement IMD is first IMD 106 without any software and/or firmware updates or that the replacement IMD is otherwise identical to first IMD 106.

Based on a determination that second IMD 108 is an old device ("NO" branch of 508), programming device 110 may complete programming of second IMD 108, e.g., by applying the same settings of first IMD 106 to second IMD 108. Based on a determination that second IMD 108 is a new device ("YES" branch of 508), programming device 110 may determine and recommend one or more settings to user (510). In some examples, as illustrated in FIG. 5, a user may wish to review the determined settings prior to implementation in second IMD 108. As such, programming device 110 may request user acceptance, via UI 302, of the one or more determined settings. Once the user accepts the one or more settings (512), programming device may then configure second IMD 108 (514) and complete programming of second IMD 108 (516), as discussed earlier.

Figure 6:
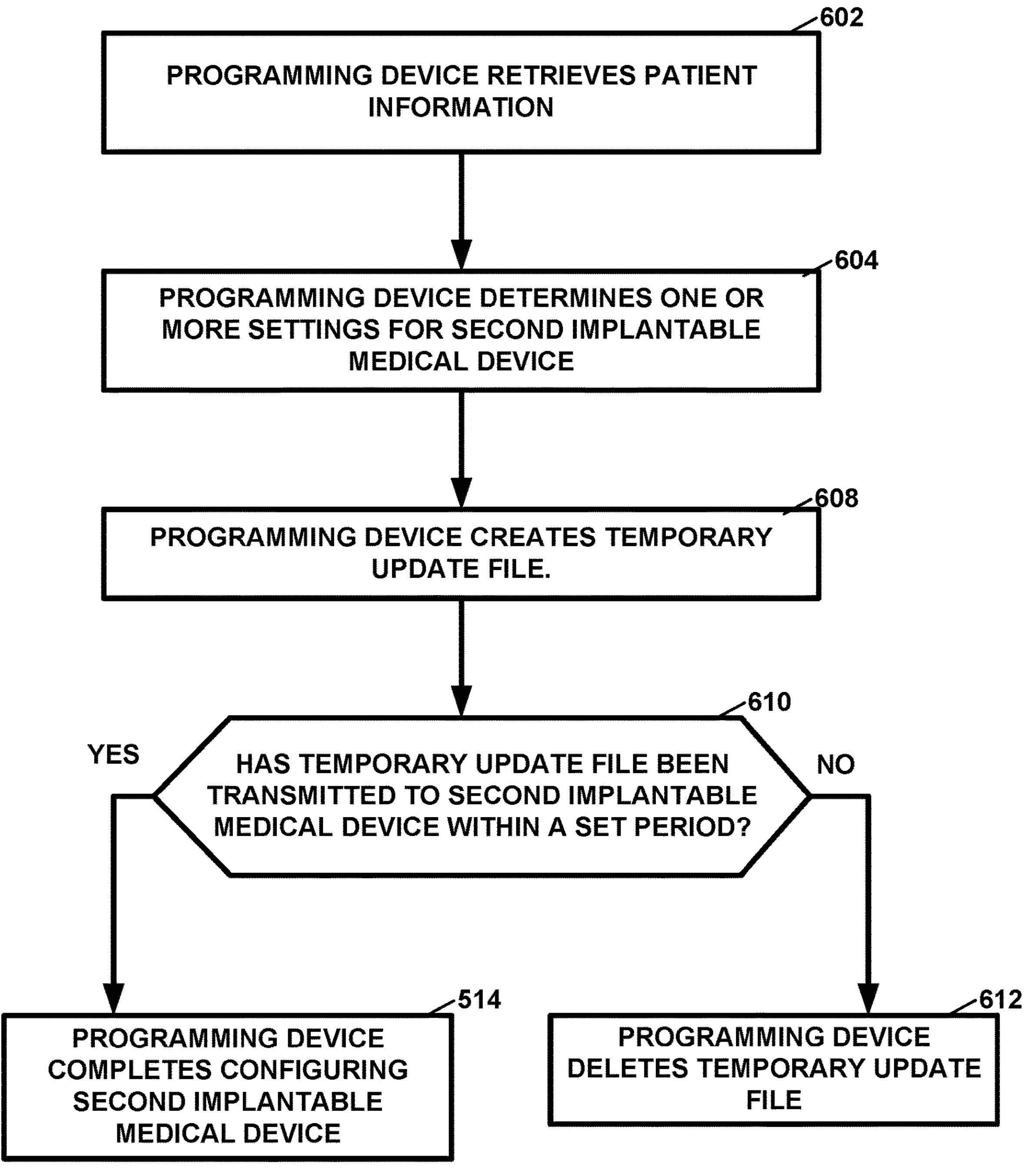
FIG. 6 is a flow chart illustrating an example method of generating a temporary update file for the second IMD based on patient information from the first IMD.

FIG. 6 is a flow chart illustrating an example method of generating a temporary update file for the second IMD 108 based on patient information from the first IMD 106. The process of generating the temporary update file may be part of determining one or more settings for second IMD 108 (506). In some examples, the process of generating the temporary update file may also be part of determining the one or more settings in the method of FIG. 4 (e.g., step 404). In some examples, generating the temporary update file may also be part of configuring second IMD 108 using the determined settings (e.g., step 406 of FIG. 4, step 514 of FIG. 5). In other examples, generating the temporary update file may be an independent step in the example methods of FIGS. 4 and 5.

Programming device 110 may retrieve patient information (e.g., from first IMD 106, a cloud computing environment, or the like) (602) and may determine one or more settings for second IMD 108 (604), e.g., in accordance with the other example methods discussed within the disclosure. Based on the one or more settings for second IMD 108, programming device 110 may generate a temporary update file (608). The temporary update file may contain portions of patient information (e.g., at least a portion of patient health parameters, changes in patient health parameters) and/or portions of device information of IMD 106. Processor 210 of second IMD 108 may be configured to determine and apply the appropriate modifications to the second set of features using the patient information stored within the temporary update file as inputs. In other examples, the temporary update file may contain instructions from processor 304 of programming device 110 to processor 210 on how to modify the second set of features. In some examples, the temporary update file may contain information in addition to information related to the modification of the second set of features. In some examples, programming device 110 may automatically attempt to transmit the temporary update file to second IMD 108 (e.g., via communications circuitry 306). In some examples, programming device 110 may store the temporary update file in memory 308 and transmit the temporary update file to second IMD 108 upon reception of instructions from user (e.g., via UI 302).

Programming device 110 may determine, after a set period of time has passed, whether the temporary update file has been transmitted to second IMD 108 (610). The set period of time may be of any chosen value (e.g., six hours). In some examples, the set period of time may be preprogramed into programming device 110. In other examples, programming device 110 may receive an input from a user (e.g., via UI 302) the value for the set period. If the temporary update file has not been transmitted to second implantable device within a set period ("NO" branch of 610), programming device 110 will delete the temporary update file (612). If the temporary update file has been transmitted to second IMD 108 ("YES" branch of 610), programming device 110 may complete configuring the second IMD 108 (514).

It should be understood that various aspects disclosed herein may be combined in different combinations than the combinations specifically presented in the description and accompanying drawings. It should be understood that, depending on the example, certain acts or events of any of the processes or methods described herein may be performed in a different sequence, may be added, merged, or left out altogether (e.g., all described acts or events may not be necessary to carry out the techniques. In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, FRAM, flash memory, or any other medium that can be used to store desired program code in the form of instructions or data structures and that can be accessed by a computer).

In addition, it should be noted that system described herein may not be limited to treatment of a human patient. In alternative examples, the system may be implemented in non-human patient, e.g., primates, canines, equines, pigs, and felines. These other animals may undergo clinical or research therapies that may benefit from the subject matter of this disclosure.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

The following is a non-limiting list of examples that may be in accordance with one or more techniques of this disclosure.

Example 1: a system for therapy upgrade, the system comprising: a memory; and processing circuitry coupled to memory, the processing circuitry being configured to: receive patient information generated with a patient having a first implantable medical device, the first implantable medical device having a first set of features; determine one or more settings for a second set of features of a second implantable medical device, wherein the second set of features are different than the first set of features; and configure the second implantable medical device based on the determined one or more settings.

Example 2: the system of example 1, wherein to determine the one or more settings for the second set of features, the processing circuitry is further configured to: determine an application of at least one of the second set of features based on the patient information; and determine the one or more of the settings to deliver the application of the at least one of the second set of features to the patient through the second implantable medical device.

Example 3: the system of any of examples 1 and 2, wherein the processing circuitry is configured to execute a machine learning model, and wherein to determine the one or more settings, the processing circuitry is configured to determine the one or more settings based on the execution of the machine learning model.

Example 4: the system of any of examples 1-3, wherein to receive the patient information, the processing circuitry is configured to receive the patient information from at least one of the first implantable medical device or a cloud computing environment.

Example 5: the system of any of examples 1-4, wherein the patient information comprises information corresponding to a health parameter of the patient.

Example 6, the system of example 5, wherein the patient information further comprises information corresponding to changes in the health parameter.

Example 7: the system of any of examples 1-6, wherein the first implantable medical device and the second implantable medical device are of a same device type.

Example 8: the system of any of examples 1-6, wherein the first implantable medical device and the second implantable medical device are of different device types.

Example 9: the system of any of examples 1-8, wherein to configure the second implantable medical device, the processing circuitry is configured to transmit the one or more settings to the second implantable medical device during implantation of the second implantable medical device into the patient.

Example 10: the system of any of examples 1-9, wherein the first implantable medical device is one of an implantable cardiac monitor (ICM) device, an implantable pulse generator (IPG) device, an implantable cardioverter defibrillator (ICD) device, or cardiac resynchronization therapy device (CRT) device, and the second implantable medical device is another of the ICM device, IPD device, ICD device, or CRT device.

Example 11: the system of any of examples 1-10, further comprising a programming device, wherein the programming device includes the processing circuitry.

Example 12: a method comprising: retrieving, by processing circuitry of a therapy upgrade system from memory of the therapy upgrade system, patient information generated with a patient having a first implantable medical device, the first implantable medical device having a first set of features; determining, by the processing circuitry, one or more settings for a second set of features of a second implantable medical device, wherein the second set of features are different than the first set of features; and configuring, by the processing circuitry, the second implantable medical device based on the determined one or more settings.

Example 13: the method of example 12, wherein determining the one or more settings for the second set of features comprises: determining, by the processing circuitry, an application of at least one of the second set of features based on the patient information; and determining, by the processing circuitry, the one or more of the settings to deliver the application of the at least one of the second set of features to the patient through the second implantable medical device.

Example 14: the method of any of examples 12 and 13, further comprising executing, by the processing circuitry, a machine learning model, and wherein determining the one or more settings comprises determining, by the processing circuitry, the one or more settings based on the execution of the machine learning model.

Example 15: the method of any of examples 12-14, wherein retrieving the patient information comprises retrieving, by the processing circuitry, the patient information from at least one of the first implantable medical device or a cloud computing environment.

Example 16: the method of any of examples 12-15, wherein the patient information comprises information corresponding to a health parameter of the patient.

Example 17: the method of example 16, wherein the patient information further comprises information corresponding to changes in the health parameter.

Example 18: the method of any of examples 12-17, wherein the first implantable medical device and the second implantable medical device are of a same device type.

Example 19: the method of any of examples 12-17, wherein the first implantable medical device and the second implantable medical device are of different device types.

Example 20: the method of any of examples 12-19, wherein configuring the second implantable medical device comprises transmitting, by the processing circuitry, one or more settings to the second implantable medical device during implantation of the second implantable medical device into the patient.

Example 21: the method of any of examples 12-20, wherein the first implantable medical device is one of an implantable cardiac monitor (ICM) device, an implantable pulse generator (IPG) device, an implantable cardioverter defibrillator (ICD) device, or cardiac resynchronization therapy (CRT) device, and the second implantable medical device is another of the ICM device, IPG device, ICD device, or CRT device.

Example 22: the method of any of examples 12-21, wherein the therapy upgrade system comprises a programming device, and wherein the programming device includes the processing circuitry.

Example 23: a computer readable storage medium comprising instructions that, when executed, cause one or more processors to perform the method of any of examples 12-22.

Example 24: a device for therapy upgrade, the device comprising: means for retrieving patient information generated with a patient having a first implantable medical device, the first implantable medical device having a first set of features; means for determining one or more settings for a second set of features of a second implantable medical device, wherein the second set of features are different than the first set of features; and means for configuring the second implantable medical device based on the determined one or more settings.

Example 25: the device of example 24, further comprising means for performing the method of any of examples 13-22.

What is claimed is:

1. A system for therapy upgrade, the system comprising:
- a memory; and
- processing circuitry coupled to the memory, the processing circuitry being configured to:
  - receive patient information generated with a patient having a first implantable medical device, the first implantable medical device having a first set of features;
  - determine one or more settings for a second set of features of a second implantable medical device, wherein the second implantable medical device is separate from the first implantable medical device, wherein the second set of features are different than the first set of features;
  - generate a temporary update file comprising instructions that, when executed by computing circuitry of the second implantable medical device, causes the second implantable medical device to configure the second set of features in accordance with the determined one or more settings;
  - save the temporary update file in the memory; and
  - delete the temporary update file from the memory based on a determination that the temporary update file has not been transmitted to the second implantable medical device after a threshold period of time.

2. The system of claim 1, wherein to determine the one or more settings for the second set of features, the processing circuitry is further configured to:
- determine an application of at least one of the second set of features based on the patient information; and
- determine the one or more of the settings to deliver the application of the at least one of the second set of features to the patient through the second implantable medical device.

3. The system of claim 1, wherein the processing circuitry is configured to execute a machine learning model, and wherein to determine the one or more settings, the processing circuitry is configured to determine the one or more settings based on the execution of the machine learning model.

4. The system of claim 1, wherein to receive the patient information, the processing circuitry is configured to receive the patient information from at least one of the first implantable medical device or a cloud computing environment.

5. The system of claim 1, wherein the patient information comprises information corresponding to a health parameter of the patient.

6. The system of claim 5, wherein the patient information further comprises information corresponding to changes in the health parameter.

7. The system of claim 1, wherein the first implantable medical device and the second implantable medical device are of a same device type, and wherein the second set of features are unavailable to the first implantable medical device.

8. The system of claim 1, wherein the first implantable medical device and the second implantable medical device are of different device types.

9. The system of claim 1, wherein the first implantable medical device is one of an implantable cardiac monitor (ICM) device, an implantable pulse generator (IPG) device, an implantable cardioverter defibrillator (ICD) device, or cardiac resynchronization therapy (CRT) device, and the second implantable medical device is another of the ICM device, IPG device, ICD device, or CRT device.

10. The system of claim 1, wherein the received information is in a first digital format, wherein the processing circuitry is further configured to:
- convert the received information from the first digital format to a second digital format, the second digital format being different than the first digital format and compatible with the second implantable medical device, and
- wherein the temporary update file further comprises the received information in the second digital format.

11. A method for therapy upgrade, the method comprising:
- retrieving, by processing circuitry of a computing system, patient information generated with a patient having a first implantable medical device, the first implantable medical device having a first set of features;
- determining, by the processing circuitry, one or more settings for a second set of features of a second implantable medical device, the second implantable medical device being separate from the first implantable medical device, wherein the second set of features are different than the first set of features;

generating, by the processing circuitry, a temporary update file comprising instructions that, when executed by computing circuitry of the second implantable medical device, causes the second implantable medical device to operate the second set of features in accordance with the determined one or more settings;

saving, by the processing circuitry, the temporary update file in memory of the computing system; and deleting, by the processing circuitry, the temporary update file from the memory based on a determination that the temporary update file has not been transmitted to the second implantable medical device after a threshold period of time.

12. The method of claim 11, wherein determining the one or more settings for the second set of features comprises:

determining, by the processing circuitry, an application of at least one of the second set of features based on the patient information; and determining, by the processing circuitry, the one or more of the settings to deliver the application of the at least one of the second set of features to the patient through the second implantable medical device.

13. The method of claim 11, further comprising executing, by the processing circuitry, a machine learning model, and wherein determining the one or more settings comprises determining, by the processing circuitry, the one or more settings based on the execution of the machine learning model.

14. The method of claim 11, wherein retrieving the patient information comprises retrieving, by the processing circuitry, the patient information from at least one of the first implantable medical device or a cloud computing environment.

15. The method of claim 11, wherein the first implantable medical device and the second implantable medical device are of a same device type, and wherein the second set of features are unavailable to the first implantable medical device.

16. The method of claim 11, wherein the first implantable medical device and the second implantable medical device are of different device types.

17. The method of claim 11, wherein the first implantable medical device is one of an implantable cardiac monitor (ICM) device, an implantable pulse generator (IPG) device, an implantable cardioverter defibrillator (ICD) device, or cardiac resynchronization therapy (CRT) device, and the second implantable medical device is another of the ICM device, IPG device, ICD device, or CRT device.

18. The method of claim 11, wherein retrieving the patient information generating with a patient having a first implantable medical device comprises:

retrieving, by the processing circuitry, the patient information in a first digital format from the first implantable medical device, and wherein the method further comprises:

converting, by the processing circuitry, the patient information from the first digital format to a second digital format, the second digital format being different than the first digital format and compatible with the second implantable medical device; and storing, by the processing circuitry, the patient information in the temporary update file in the second digital format.

19. A computer readable storage medium comprising instructions that, when executed, cause one or more processors of a computing system to:

retrieve patient information generated with a patient having a first implantable medical device, the first implantable medical device having a first set of features;

determine one or more settings for a second set of features of a second implantable medical device, the second implantable medical device being separate from the first implantable medical device, wherein the second set of features are different than the first set of features;

generate a temporary update file comprising instructions that, when executed by computing circuitry of the second implantable medical device, causes the second implantable medical device to operate the second set of features in accordance with the determined one or more settings;

save the temporary update file in memory of the computing system; and delete the temporary update file from the memory based on a determination that the temporary update file has not been transmitted to the second implantable medical device after a threshold period of time.

20. The computer readable storage medium of claim 19, wherein the retrieved patient information is in a first digital format, and wherein the computer readable storage medium further comprises instructions that, when executed, causes the one or more processors to:

convert the patient information from the first digital format to a second digital format, the second digital format being different than the first digital format and compatible with the second implantable medical device; and store the patient information in the temporary update file in the second digital format.

* * * * *